United States Patent [19]
Skatrud et al.

[11] Patent Number: 5,776,733
[45] Date of Patent: Jul. 7, 1998

[54] **BIOSYNTHETIC GENE DD1 FROM *STREPTOCOCCUS PNEUMONIAE***

[75] Inventors: Paul L. Skatrud, Indianapolis; Robert B. Peery, Brownsburg, both of Ind.

[73] Assignee: Eli Lilly and Company, Indianapolis, Ind.

[21] Appl. No.: 690,413

[22] Filed: Jul. 25, 1996

[51] Int. Cl.$^6$ .............. C12N 1/21; C12N 15/63; C12N 9/00; C07K 14/315

[52] U.S. Cl. ............. 435/69.1; 435/172.3; 435/183; 435/252.3; 435/252.33; 435/320.1; 536/23.2; 536/23.7

[58] Field of Search ............ 435/320.1, 252.33, 435/252.3, 172.3, 183, 69.1; 536/23.7, 23.2

[56] References Cited

PUBLICATIONS

Fischer et al., J. Bacteriol., 163(1):46–54, 1985.
Evers et al., Gene, 140: 97–102, 1994.
Navarro et al., Antimicrob. Agents and Chemotherapy, 38, (8): 1788–1793, Aug. 1994.
Daub et al., Biochemistry, 27:3701–3708, 1988.
Al–BaR et al., Biochem. J., 282:747–752, 1992.
Daub et al. "Isolation, Cloning and Sequencing . . . " Biochem. 27, 3701–3708 (1988).
Greenlee et al. "Synthesis of an Analogue of Tabtoxinine as potential inhib. of alanine:alanine ligase" J. Med. Chem. 32, 165–170 (1989).
Zawadzke et al. "Existence of Two D–alanine . . . " Biochem. 30, 1673–1682 (1991).

*Primary Examiner*—Johnny F. Railey, II
*Attorney, Agent, or Firm*—Thomas D. Webster; David E. Boone

[57] ABSTRACT

The invention provides isolated nucleic acid compounds encoding the stem peptide biosynthetic gene ddl of *Streptococcus pneumoniae*. Also provided are vectors and transformed heterologous host cells for expressing the DDL enzyme product and a method for identifying compounds that inhibit stem peptide biosynthesis.

10 Claims, 1 Drawing Sheet

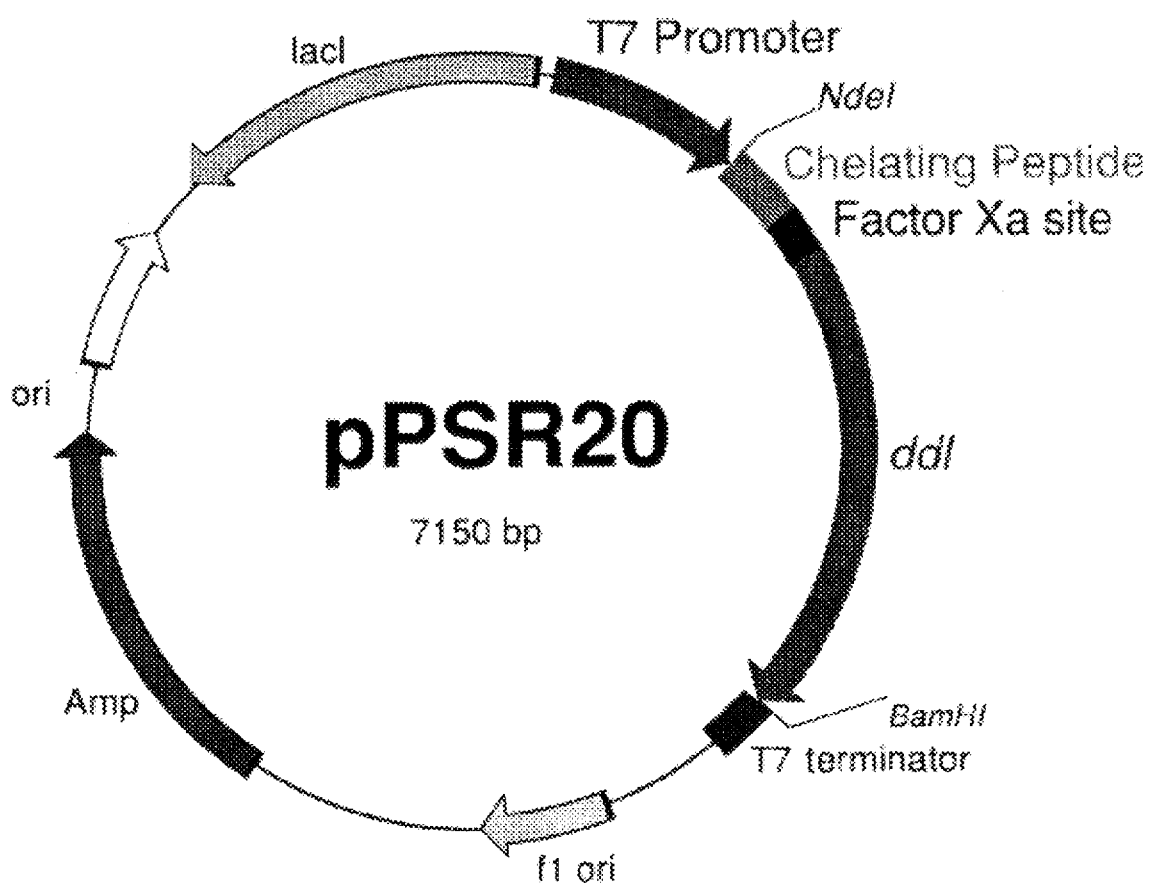
Figure

BIOSYNTHETIC GENE DD1 FROM *STREPTOCOCCUS PNEUMONIAE*

BACKGROUND OF THE INVENTION

This invention relates to recombinant DNA technology. In particular the invention pertains to the cloning of the ddl gene encoding D-alanine:D-alanine ligase of *Streptococcus pneumoniae* and the use of the ddl. gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that compounds that interfere with cell wall biosynthesis have low toxicity in humans and potentially high therapeutic value.

The bacterial cell wall structure contains a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide." or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is the peptidoglycan crosslinking step that has been a frequently targeted site for antibiotic compounds such as the beta-lactam antibiotics.

Unlike the widely targeted peptidoglycan crosslinking step, the stem peptide pathway has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by UDP-N-acetylmuramate:L-alanine ligase; UDP-N-acetyl-muramyl-L-alanine:D-glutamate ligase; UDP-N-acetyl-muramyl-L-alanyl-D-isoglutamate:L-lysine ligase; UDP-N-acetylmuramyl-L-alanyl-D-isoglutamyl-L-lysine:D-alanyl-D-alanine ligase; and D-alanyl-D-alanine ligase, the final product, UDPMurNAc-L-Ala-D-isoGlu-L-lysine-D-Ala-D-Ala, is produced in *Streptococcus pneumoniae*.

The enzymatic steps involved in the formation of the stem peptide are potential targets for new antibacterial agents. A few inhibitors, which target this pathway, have been developed. For example, D-cycloserine inhibits alanine racemase and D-alanine-D-alanine ligase; phosphonomycin inhibits the conversion of UDP-GlcNAc to UDP-GlcNac- enolpyruvate; and Ala-phosphonine inhibits the formation of UDP-MurNac-L-Ala.

While inroads in the development of new antibiotics and new targets for antibiotic compounds have emerged in a variety of microorganisms, progress has been less apparent in *Streptococcus pneumoniae*. In part, *Streptococcus pneumoniae* presents a special case because this organism is highly mutagenic and readily takes up exogenous DNA from its surroundings. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the ddl gene product from *Streptococcus pneumoniae*. The invention also provides the protein product of the *Streptococcus pneumoniae* ddl gene, D-alanine:D-alanine ligase (DDL protein), in substantially purified form.

Having the cloned ddl gene of *Streptococcus pneumoniae* enables the production of recombinant DDL protein and the implementation of large scale screens to identify new inhibitory compounds targeted at the stem peptide biosynthetic pathway. It may be possible to combine stem peptide proteins in a single screen to examine several steps at the same time. Structural analysis of the DDL protein will enable structure-based drug design to develop novel compounds effective in the treatment of antibiotic resistant microorganisms.

In one embodiment the present invention relates to an isolated DNA molecule encoding DDL protein, said DNA molecule comprising the nucleotide sequence identified as SEQ ID NO. 1:

| | | | | | | |
|---|---|---|---|---|---|---|
| ATGAAACAAA | CGATTATTCT | TTTATATGGT | GGACGGAGTG | CGGAACGCGA | AGTCTCTGTC | 60 |
| CTTTCAGCTG | AGAGTGTCAT | GCGTGCGGTC | GATTACGACC | GTTTCACAGT | CAAGACTTTC | 120 |
| TTTATCAGTC | AGTCAGGTGA | CTTTATCAAA | ACACAGGAAT | TTAGTCATGC | TCCGGGGCAA | 180 |
| GAAGACCGTC | TCATGACCAA | TGAAACCATT | GATTGGGATA | AGAAAGTTGC | ACCAAGTGCT | 240 |
| ATCTACGAAG | AAGGTGCAGT | GGTCTTTCCA | GTCCTTCACG | GGCCAATGGG | AGAAGATGGC | 300 |
| TCTGTTCAAG | GATTCTTGGA | AGTTTTGAAA | ATGCCTTACG | TTGGTTGCAA | CATTTTGTCA | 360 |
| TCAAGTCTTG | CCATGGATAA | AATCACGACT | AAGCGTGTTC | TGGAATCTGC | TGGTATTGCC | 420 |
| CAAGTTCCTT | ATGTGGCTAT | CGTTGAAGGC | GATGATGTGA | CTGCTAAAAT | CGCTGAAGTG | 480 |
| GAAGAAAAAT | TGGCTTATCC | AGTCTTCACT | AAGCCGTCAA | ACATGGGGTC | TAGTGTCGGT | 540 |
| ATTTCTAAGT | CTGAAAACCA | AGAAGAACTC | CGTCAAGCCT | TAAAACTTGC | CTTCCGATAT | 600 |
| GACAGCCGTG | TCTTGGTTGA | GCAAGGAGTG | AATGCCCGTG | AAATTGAGGT | TGGCCTCTTG | 660 |
| GGTAACTACG | ATGTCAAGAG | CACGCTACCT | GGAGAAGTTG | TCAAGGACGT | TGCCTTTTAT | 720 |
| GACTACGATG | CCAAGTATAT | TGATAACAAG | GTTACTATGG | ATATTCCTGC | CAAAATCAGT | 780 |
| GATGATGTGG | TGGCTGTCAT | GCGTCAAAAT | GCAGAAACAG | CCTTCCGTGC | CATTGGTGGC | 840 |
| CTTGGTCTAT | CTCGTTGCGA | TTTCTTCTAT | ACAGATAAGG | GAGAGATTTT | TCTCAACGAG | 900 |

| | | | | | | |
|---|---|---|---|---|---|---|
| CTCAATACCA | TGCCAGGTTT | CACCCAGTGG | TCTATGTACC | CACTACTTTG | GGAAAATATG | 960 |
| GGGATCAGCT | ACCCAGAACT | AATCGAGCGT | TTGGTTGACC | TTGCCAAGGA | AAGTTTTGAC | 1020 |
| AAGCGCGAAG | CGCATTTGAT | A | | | | 1041 |

In another embodiment the present invention relates to a DDL protein molecule, wherein said protein molecule comprises the sequence identified as SEQ ID NO. 2.

In a further embodiment the present invention relates to a ribonucleic acid molecule encoding DDL protein, said ribonucleic acid molecule comprising the sequence identified as SEQ ID NO. 3:

In yet another embodiment, the present invention relates to a recombinant DNA vector which incorporates the *Streptococcus pneumoniae* ddl gene in operable linkage to gene expression sequences enabling the ddl gene to be transcribed and translated in a host cell.

In still another embodiment the present invention relates to homologous or heterologous host cells which have been transformed or transfected with the cloned ddl gene of *Streptococcus pneumoniae* such that the ddl gene is expressed in the host cell.

In a still further embodiment, the present invention relates to a method for identifying compounds that inhibit the enzymatic activity of the DDL protein of *Streptococcus pneumoniae*.

DESCRIPTION OF THE DRAWING

Figure. Plasmid pPSR20 useful for high level expression of the *Streptococcus pneumoniae* ddl gene in the heterologous procaryotic host cell *Eschericia coli*.

DEFINITIONS

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"DDL" refers to the protein encoded by ddl, D-alanine-D-alanine Ligase.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non- homologous basepairing. Low stringency conditions have the opposite effect. Stringency may be altered, for example, by temperature and salt concentration.

DETAILED DESCRIPTION

The ddl gene of *Streptococcus pneumoniae* encodes an enzyme involved in stem peptide biosynthesis. The stem peptide pathway is necessary for the synthesis of the peptidoglycan layer, which is part of the bacterial cell wall. There are at least 10 steps involved in stem peptide biosynthesis. The ddl gene encodes D-alanine:D-alanine Ligase (SEQ ID NO. 2), which catalyzes the ATP-dependent ligation of two molecules of D-alanine.

The ddl gene of *Streptococcus pneumoniae* comprises a DNA sequence of 1041 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recognize that the ddl gene may be obtained by a plurality of applicable genetic and recombinant DNA techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J.Sambrook et al. Supra]. Suitable cloning vectors are widely available. Skilled artisans will recognize that the ddl gene of *Streptococcus pneumoniae* or fragment thereof could be isolated by PCR amplification of *Streptococcus pneumoniae* genomic DNA or CDNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified protein encoded by the ddl gene or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Biooraanic Chemistry* (1981) Springer-Verlag, N.Y., 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20° C. for thirty minutes followed by thirty minutes at 0° C.

The protein of the present invention can also be produced by recombinant DNA methods using the cloned ddl gene of *Streptococcus pneumoniae*. Recombinant methods are preferred if a high yield is desired. Expression of the cloned ddl gene can be carried out in a variety of suitable host cells well known to those skilled in the art. The ddl gene is introduced into a host cell by any suitable means, well known to those skilled in the art. While chromosomal integration of the cloned ddl gene is within the scope of the present invention, it is preferred that the gene be cloned into a suitable extra-chromosomally maintained expression vector so that the coding region of the ddl gene is operably linked to a constitutive or inducible promoter.

The basic steps in the recombinant production of the DDL protein are:

a) constructing a natural, synthetic or semi-synthetic DNA encoding DDL protein;

b) integrating said DNA into an expression vector in a manner suitable for expressing the DDL protein, either alone or as a fusion protein;

c) transforming or otherwise introducing said vector into an appropriate eucaryotic or prokaryotic host cell forming a recombinant host cell, d) culturing said recombinant host cell in a manner to express the DDL protein; and e) recovering and purifying the DDL protein by any suitable means, well known to those skilled in the art.

Expressing Recombinant DDL Protein in Procarvotic and Eucarvotic Host Cells

In general, procaryotes are used for cloning DNA sequences and for constructing the vectors of the present invention. Procaryotes are also employed in the production of the DDL protein. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Larae Scale Processes*, American Chemical Society, Washington, D.C. (1990).

In addition to procaryotes, mammalian host cells and eucaryotic microbes such as yeast may also be used. The simple eucaryote *Saccharomyces cerevisiae*, is the most commonly used eucaryotic microorganism, although a number of other yeasts such as *Kluyveromyces lactis* are also suitable. For expression in Saccharomyces, the plasmid YRp7 (ATCC- 40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced DDL Protein

An expression vector carrying the cloned ddl gene of *Streptococcus pneumoniae* is transformed or transfected into a suitable host cell using standard methods. Cells which contain the vector are then propagated under conditions suitable for expression of the DDL protein. If the gene is under the control of an inducible promoter then synthetic growth conditions would incorporate the appropriate inducer. The recombinantly produced protein may be purified from cellular extracts of transformed host cells by any suitable means. [See generally e.g. T. Maniatis et al. *Molecular Cloning*, 1982 Cold Spring Harbor; Methods in Enzymology, Vol. 152, Guide to Molecular Cloning Techniques, Eds. S. Berger and A. Kimmel, 1987, Academic Press]. In a preferred process for protein purification the ddl gene is modified at the 5' end to incorporate several histidine residues at the amino terminus of the DDL protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure DDL protein.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one codon due to the degeneracy of the genetic code. Because these alternative nucleic acid sequences would encode the same amino acid sequences, the present invention further comprises these alternate nucleic acid sequences.

The ddl gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the ddl gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Olia-onucleotide Synthesis, A Practical Approach*, (1984).]

In an alternative methodology, namely PCR, the ddl DNA sequence comprising a portion or all of SEQ ID NO:1 can be generated from *Streptococcus pneumoniae* genomic DNA using suitable oligonucleotide primers complementary to SEQ ID NO:1 or region therein, as described in U.S. Pat. No. 4,889,818, which is incorporated herein by reference. Suitable protocols for performing the PCR are disclosed in, *PCR Protocols: A Guide to Method and Applications*, Ed. Michael A. Innis et al., Academic Press, Inc. (1990), which hereby is incorporated by reference.

The ribonucleic acids of the present invention may be prepared using the polynucleotide synthetic methods discussed supra, or they may be prepared enzymatically using RNA polymerase to transcribe a ddl DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5'end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Streptococcus pneumoniae* DNA or mRNA encoding ddl, is provided. Preferably, the 18 or more base pair compound is DNA.

These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1. Plasmid PPSR20 is an especially preferred DNA vector of the present invention.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters which respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* which has been transfected or transformed with a vector which comprises the nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. The preferred host cell is any strain of *E. coli* which can accomodate high level expression of an exogenously introduced gene. Preferred vectors for expression are those which comprise SEQ ID NO:1. An especially preferred expression vector for use in *E. coli* is plasmid pPSR20, which comprises SEQ ID NO:1. (See Figure). Transformed host cells may be cultured under conditions well known to skilled artisans such that SEQ ID NO:2 is expressed, thereby producing DDL protein in the recombinant host cell.

For the purpose of identifying or developing inhibitors of the stem peptide pathway, it would be desirable to determine those agents which inhibit the DDL step. A method for determining whether a substance will inhibit the enzymatic reaction catalyzed by the DDL protein comprises contacting the DDL protein with a test inhibitory compound and monitoring DDL enzyme activity by any suitable means.

The instant invention provides such a screening system useful for discovering compounds which inhibit the DDL protein, said screening system comprising the steps of:

a) preparing DDL enzyme;

b) exposing said DDL enzyme to a test inhibitor;

c) introducing a specific DDL substrate; and d) quantifying the loss of activity of said DDL enzyme.

Utilization of the screening system described above provides a means to determine compounds which interfere with stem peptide biosynthesis. This screening method may be adapted to automated procedures such as a PANDEX® (Baxter- Dade Diagnostics) system, allowing for efficient high-volume screening of potential therapeutic agents.

In such a screening protocol DDL enzyme is prepared as described herein, preferably using recombinant DNA technology. A test inhibitory compound is then introduced into the reaction vessel containing the DDL enzyme, followed by addition of enzyme substrate. Alternatively, substrate may be added simultaneously with the test compound. For example, in a preferred method radioactively or chemically-labeled substrate may be used. The products of the enzymatic reaction are assayed for the chemical label or radioactivity by any suitable means. The absence or diminution of the chemical label or radioactivity indicates the degree to which the reaction is inhibited. The DDL enzyme utilizes D-alanine and ATP as substrates. A variety of suitable assays for DDL enzyme activity are available for use in the instant invention. See e.g. E. Daub et al. Biochem. 27, 3701 (1988).

Skilled artisans will recognize that $IC_{50}$ values are dependent on the selectivity of the compound tested. For example, a compound with an $IC_{50}$ which is less than 10 nM is generally considered an excellent candidate for drug therapy.

However, a compound which has a lower affinity, but is selective for a particular target, may be an even better candidate. The skilled artisan will recognize that any information regarding inhibitory activity or selectivity of a particular compound is beneficial in the pharmaceutical arts.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Streptococcus pnuemoniae* ddl Gene in a Homologous or Heterologous Host Plasmid pPSR20 (See Figure) is an approximately 7150 base pair expression vector suitable for expressing the ddl gene of *S. pneumoniae* in the procaryotic host *E. coli*. This plasmid contains an origin of replication (Ori), an ampicillin resistance gene (Amp), useful for selecting cells which have incorporated the vector following a tranformation procedure, and further comprises the lacI gene for repression of the lac operon, as well as the T7 promoter and T7 terminator sequences in operable linkage to the coding region of the ddl gene. Parent plasmid pET11A (obtained from Novogen, Madison, Wis.) was linearized by digestion with endonucleases NdeI and BamHI. Linearized PET11A was ligated to a DNA fragment bearing NdeI and BamHI sticky ends and further comprising the coding region of the *S. pneumoniae* ddl gene.

The ddl gene, which was ligated into pPSR20, was modified at the 5' end (amino terminus of encoded protein) in order to simplify purification of the encoded DDL protein product. For this purpose, an oligonucleotide encoding 8 histidine residues and a factor Xa cleavage site was inserted after the ATG start codon at nucleotide positions 1 to 3 of SEQ ID NO: 1. Placement of the histidine residues at the amino terminus of the encoded protein does not affect its activity and serves only to enable the IMAC one-step protein purification procedure (See below).

EXAMPLE 2

Expression of *Streptococcus pneumoniae* ddl Gene in *Echerichia coli* and Purification of DDL Enzyme Plasmid pPSR20 is transformed into *E. coli* BL21 (DE3) (hsdS gal λcIts857 ind1Sam7nin5acUV5-T7gene 1) using standard methods (See e.g. Sambrook et al (supra). Transformants, selected for resistance to ampicillin, are chosen at random and tested for the presence of pPSR20 by agarose gel electrophoresis using quick plasmid preparations. Id. Colonies that contain pPSR20 are grown, processed, and the protein product encoded by the ddl gene purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract prepared from a recombinant host transformed or transfected with plasmid pPSR20.

After washing the column with a suitable buffer, pH 7.5 to remove unbound proteins and other materials, the bound recombinant DDL protein is eluted in a buffer at pH 4.3, essentially as described in U.S. Pat. No. 4,569,794.

EXAMPLE 3

Biochemical Assay for Inhibitors of *Streptococcus pneumoniae* DDL Enzyme Product The activity of the DDL enzyme is assayed by a colorimetric assay that monitors D-alanine-dependent release of $P_i$ from ATP. The incubation mixture (50 μl) conists of 25 mM HEPES, pH 7.8, 10 mM $MgCl_2$, 10 mM KCl, 2 mM ATP, and 10 mM D-alanine, plus enzyme. The mixture is added to 0.8 ml of a colorimetric reagent according to the method of Lanzetta et al. [Anal. Biochem. 100, 95–97 (1979)].

Inhibition studies are carried out using the reaction conditions described in the preceding paragraph. Test inhibitory compounds are added to a final concentration of between 1 mM and 10 mM, and the percentage inhibition of the DDL enzyme reaction ascertained by comparison with a control in which no test inhibitor is present.

We claim:

1. An isolated nucleic acid compound consisting of a compound encoding the protein having the amino acid sequence which is SEQ ID NO 2.

2. An isolated nucleic acid compound comprising a sequence encoding the protein of SEQ ID NO. 2, wherein said compound has a sequence selected from the group consisting of:

(a)

| | | | | | | |
|---|---|---|---|---|---|---|
| ATGAAACAAA | CGATTATTCT | TTTATATGGT | GGACGGAGTG | CGGAACGCGA | AGTCTCTGTC | 60 |
| CTTTCAGCTG | AGAGTGTCAT | GCGTGCGGTC | GATTACGACC | GTTTCACAGT | CAAGACTTTC | 120 |
| TTTATCAGTC | AGTCAGGTGA | CTTTATCAAA | ACACAGGAAT | TTAGTCATGC | TCCGGGCAA | 180 |
| GAAGACCGTC | TCATGACCAA | TGAAACCATT | GATTGGGATA | AGAAAGTTGC | ACCAAGTGCT | 240 |
| ATCTACGAAG | AAGGTGCAGT | GGTCTTTCCA | GTCCTTCACG | GGCCAATGGG | AGAAGATGGC | 300 |
| TCTGTTCAAG | GATTCTTGGA | AGTTTTGAAA | ATGCCTTACG | TTGGTTGCAA | CATTTTGTCA | 360 |
| TCAAGTCTTG | CCATGGATAA | AATCACGACT | AAGCGTGTTC | TGGAATCTGC | TGGTATTGCC | 420 |
| CAAGTTCCTT | ATGTGGCTAT | CGTTGAAGGC | GATGATGTGA | CTGCTAAAAT | CGCTGAAGTG | 480 |
| GAAGAAAAAT | TGGCTTATCC | AGTCTTCACT | AAGCCGTCAA | ACATGGGGTC | TAGTGTCGGT | 540 |
| ATTTCTAAGT | CTGAAAACCA | AGAAGAACTC | CGTCAAGCCT | TAAAACTTGC | CTTCCGATAT | 600 |
| GACAGCCGTG | TCTTGGTTGA | GCAAGGAGTG | AATGCCCGTG | AAATTGAGGT | TGGCCTCTTG | 660 |
| GGTAACTACG | ATGTCAAGAG | CACGCTACCT | GGAGAAGTTG | TCAAGGACGT | TGCCTTTTAT | 720 |
| GACTACGATG | CCAAGTATAT | TGATAACAAG | GTTACTATGG | ATATTCCTGC | CAAAATCAGT | 780 |
| GATGATGTGG | TGGCTGTCAT | GCGTCAAAAT | GCAGAAACAG | CCTTCCGTGC | CATTGGTGGC | 840 |
| CTTGGTCTAT | CTCGTTGCGA | TTTCTTCTAT | ACAGATAAGG | GAGAGATTTT | TCTCAACGAG | 900 |
| CTCAATACCA | TGCCAGGTTT | CACCCAGTGG | TCTATGTACC | CACTACTTTG | GGAAAATATG | 960 |
| GGGATCAGCT | ACCCAGAACT | AATCGAGCGT | TTGGTTGACC | TTGCCAAGGA | AAGTTTTGAC | 1020 |
| AAGCGCGAAG | CGCATTTGAT | A | | | | 1041 | which is SEQ ID NO:1;

(b)

| | | | | | | |
|---|---|---|---|---|---|---|
| AUGAAACAAA | CGAUUAUUCU | UUUAUAUGGU | GGACGGAGUG | CGGAACGCGA | AGUCUCUGUC | 60 |
| CUUUCAGCUG | AGAGUGUCAU | GCGUGCGGUC | GAUUACGACC | GUUUCACAGU | CAAGACUUUC | 120 |
| UUUAUCAGUC | AGUCAGGUGA | CUUUAUCAAA | ACACAGGAAU | UUAGUCAUGC | UCCGGGCAA | 180 |
| GAAGACCGUC | UCAUGACCAA | UGAAACCAUU | GAUUGGGAUA | AGAAAGUUGC | ACCAAGUGCU | 240 |
| AUCUACGAAG | AAGGUGCAGU | GGUCUUUCCA | GUCCUUCACG | GGCCAAUGGG | AGAAGAUGGC | 300 |
| UCUGUUCAAG | GAUUCUUGGA | AGUUUUGAAA | AUGCCUUACG | UUGGUUGCAA | CAUUUUGUCA | 360 |
| UCAAGUCUUG | CCAUGGAUAA | AAUCACGACU | AAGCGUGUUC | UGGAAUCUGC | UGGUAUUGCC | 420 |
| CAAGUUCCUU | AUGUGGCUAU | CGUUGAAGGC | GAUGAUGUGA | CUGCUAAAAU | CGCUGAAGUG | 480 |

-continued

| | | | | | | |
|---|---|---|---|---|---|---|
| GAAGAAAAAU | UGGCUUAUCC | AGUCUUCACU | AAGCCGUCAA | ACAUGGGGUC | UAGUGUCGGU | 540 |
| AUUUCUAAGU | CUGAAAACCA | AGAAGAACUC | CGUCAAGCCU | UAAAACUUGC | CUUCCGAUAU | 600 |
| GACAGCCGUG | UCUUGGUUGA | GCAAGGAGUG | AAUGCCCGUG | AAAUUGAGGU | UGGCCUCUUG | 660 |
| GGUAACUACG | AUGUCAAGAG | CACGCUACCU | GGAGAAGUUG | UCAAGGACGU | UGCCUUUUAU | 720 |
| GACUACGAUG | CCAAGUAUAU | UGAUAACAAG | GUUACUAUGG | AUAUUCCUGC | CAAAAUCAGU | 780 |
| GAUGAUGUGG | UGGCUGUCAU | GCGUCAAAAU | GCAGAAACAG | CCUUCCGUGC | CAUUGGUGGC | 840 |
| CUUGGUCUAU | CUCGUUGCGA | UUUCUUCUAU | ACAGAUAAGG | GAGAGAUUUU | UCUCAACGAG | 900 |
| CUCAAUACCA | UGCCAGGUUU | CACCCAGUGG | UCUAUGUACC | CACUACUUUG | GGAAAAUAUG | 960 |
| GGGAUCAGCU | ACCCAGAACU | AAUCGAGCGU | UUGGUUGACC | UUGCCAAGGA | AAGUUUUGAC | 1020 |
| AAGCGCGAAG | CGCAUUUGAU | A | | | | 1041 | which is SEQ ID NO:3;

(c) a nucleic acid compound complementary to (a) or (b); and (d) a fragment of (a), (b), or (c) that is at least 18 base pairs in length and which will selectively hybridize to ddl genomic DNA.

3. An isolated nucleic acid compound of claim 2 wherein the sequence of said compound is SEQ ID NO:1 or a sequence complementary to SEQ ID.NO:1.

4. An isolated nucleic acid compound of claim 2 wherein the sequence of said compound is SEQ ID NO:3 or a sequence complementary to SEQ ID NO:3.

5. A vector comprising an isolated nucleic acid compound of claim 2.

6. The vector of claim 5, wherein said isolated nucleic acid compound is SEQ ID NO 1 operably linked to a promoter sequence.

7. A host cell containing the vector of claim 5.

8. A host cell containing the vector of claim 6.

9. A method for constructing a recombinant host cell having the potential to express SEQ ID NO:2, said method comprising introducing into said host cell by any suitable means a vector of claim 6.

10. A method for expressing SEQ ID NO:2 in the recombinant host cell of claim 9, said method comprising culturing said recombinant host cell under conditions suitable for gene expression.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1041 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1041

( x i ) SEQUENCE DESCRIPTION: SEQ ID NO:1:

```
ATG AAA CAA ACG ATT ATT CTT TTA TAT GGT GGA CGG AGT GCG GAA CGC         48
Met Lys Gln Thr Ile Ile Leu Leu Tyr Gly Gly Arg Ser Ala Glu Arg
 1               5                  10                  15

GAA GTC TCT GTC CTT TCA GCT GAG AGT GTC ATG CGT GCG GTC GAT TAC         96
Glu Val Ser Val Leu Ser Ala Glu Ser Val Met Arg Ala Val Asp Tyr
             20                  25                  30

GAC CGT TTC ACA GTC AAG ACT TTC TTT ATC AGT CAG TCA GGT GAC TTT        144
Asp Arg Phe Thr Val Lys Thr Phe Phe Ile Ser Gln Ser Gly Asp Phe
         35                  40                  45

ATC AAA ACA CAG GAA TTT AGT CAT GCT CCG GGG CAA GAA GAC CGT CTC        192
Ile Lys Thr Gln Glu Phe Ser His Ala Pro Gly Gln Glu Asp Arg Leu
     50                  55                  60

ATG ACC AAT GAA ACC ATT GAT TGG GAT AAG AAA GTT GCA CCA AGT GCT        240
Met Thr Asn Glu Thr Ile Asp Trp Asp Lys Lys Val Ala Pro Ser Ala
 65                  70                  75                  80

ATC TAC GAA GAA GGT GCA GTG GTC TTT CCA GTC CTT CAC GGG CCA ATG        288
Ile Tyr Glu Glu Gly Ala Val Val Phe Pro Val Leu His Gly Pro Met
                 85                  90                  95

GGA GAA GAT GGC TCT GTT CAA GGA TTC TTG GAA GTT TTG AAA ATG CCT        336
Gly Glu Asp Gly Ser Val Gln Gly Phe Leu Glu Val Leu Lys Met Pro
                100                 105                 110

TAC GTT GGT TGC AAC ATT TTG TCA TCA AGT CTT GCC ATG GAT AAA ATC        384
Tyr Val Gly Cys Asn Ile Leu Ser Ser Ser Leu Ala Met Asp Lys Ile
            115                 120                 125

ACG ACT AAG CGT GTT CTG GAA TCT GCT GGT ATT GCC CAA GTT CCT TAT        432
Thr Thr Lys Arg Val Leu Glu Ser Ala Gly Ile Ala Gln Val Pro Tyr
```

-continued

|     |     |     |     |     | 130 |     |     |     |     | 135 |     |     |     |     | 140 |     |      |
|-----|-----|-----|-----|-----|-----|-----|-----|-----|-----|-----|-----|-----|-----|-----|-----|-----|------|
| GTG | GCT | ATC | GTT | GAA | GGC | GAT | GAT | GTG | ACT | GCT | AAA | ATC | GCT | GAA | GTG |     | 480  |
| Val | Ala | Ile | Val | Glu | Gly | Asp | Asp | Val | Thr | Ala | Lys | Ile | Ala | Glu | Val |     |      |
| 145 |     |     |     |     | 150 |     |     |     |     | 155 |     |     |     |     | 160 |     |      |
| GAA | GAA | AAA | TTG | GCT | TAT | CCA | GTC | TTC | ACT | AAG | CCG | TCA | AAC | ATG | GGG |     | 528  |
| Glu | Glu | Lys | Leu | Ala | Tyr | Pro | Val | Phe | Thr | Lys | Pro | Ser | Asn | Met | Gly |     |      |
|     |     |     |     | 165 |     |     |     |     | 170 |     |     |     |     | 175 |     |     |      |
| TCT | AGT | GTC | GGT | ATT | TCT | AAG | TCT | GAA | AAC | CAA | GAA | GAA | CTC | CGT | CAA |     | 576  |
| Ser | Ser | Val | Gly | Ile | Ser | Lys | Ser | Glu | Asn | Gln | Glu | Glu | Leu | Arg | Gln |     |      |
|     |     |     | 180 |     |     |     |     | 185 |     |     |     |     | 190 |     |     |     |      |
| GCC | TTA | AAA | CTT | GCC | TTC | CGA | TAT | GAC | AGC | CGT | GTC | TTG | GTT | GAG | CAA |     | 624  |
| Ala | Leu | Lys | Leu | Ala | Phe | Arg | Tyr | Asp | Ser | Arg | Val | Leu | Val | Glu | Gln |     |      |
|     |     | 195 |     |     |     |     | 200 |     |     |     |     | 205 |     |     |     |     |      |
| GGA | GTG | AAT | GCC | CGT | GAA | ATT | GAG | GTT | GGC | CTC | TTG | GGT | AAC | TAC | GAT |     | 672  |
| Gly | Val | Asn | Ala | Arg | Glu | Ile | Glu | Val | Gly | Leu | Leu | Gly | Asn | Tyr | Asp |     |      |
|     | 210 |     |     |     |     | 215 |     |     |     |     | 220 |     |     |     |     |     |      |
| GTC | AAG | AGC | ACG | CTA | CCT | GGA | GAA | GTT | GTC | AAG | GAC | GTT | GCC | TTT | TAT |     | 720  |
| Val | Lys | Ser | Thr | Leu | Pro | Gly | Glu | Val | Val | Lys | Asp | Val | Ala | Phe | Tyr |     |      |
| 225 |     |     |     |     | 230 |     |     |     |     | 235 |     |     |     |     | 240 |     |      |
| GAC | TAC | GAT | GCC | AAG | TAT | ATT | GAT | AAC | AAG | GTT | ACT | ATG | GAT | ATT | CCT |     | 768  |
| Asp | Tyr | Asp | Ala | Lys | Tyr | Ile | Asp | Asn | Lys | Val | Thr | Met | Asp | Ile | Pro |     |      |
|     |     |     |     | 245 |     |     |     |     | 250 |     |     |     |     | 255 |     |     |      |
| GCC | AAA | ATC | AGT | GAT | GAT | GTG | GTG | GCT | GTC | ATG | CGT | CAA | AAT | GCA | GAA |     | 816  |
| Ala | Lys | Ile | Ser | Asp | Asp | Val | Val | Ala | Val | Met | Arg | Gln | Asn | Ala | Glu |     |      |
|     |     |     | 260 |     |     |     |     | 265 |     |     |     |     | 270 |     |     |     |      |
| ACA | GCC | TTC | CGT | GCC | ATT | GGT | GGC | CTT | GGT | CTA | TCT | CGT | TGC | GAT | TTC |     | 864  |
| Thr | Ala | Phe | Arg | Ala | Ile | Gly | Gly | Leu | Gly | Leu | Ser | Arg | Cys | Asp | Phe |     |      |
|     |     | 275 |     |     |     |     | 280 |     |     |     |     | 285 |     |     |     |     |      |
| TTC | TAT | ACA | GAT | AAG | GGA | GAG | ATT | TTT | CTC | AAC | GAG | CTC | AAT | ACC | ATG |     | 912  |
| Phe | Tyr | Thr | Asp | Lys | Gly | Glu | Ile | Phe | Leu | Asn | Glu | Leu | Asn | Thr | Met |     |      |
|     | 290 |     |     |     |     | 295 |     |     |     |     | 300 |     |     |     |     |     |      |
| CCA | GGT | TTC | ACC | CAG | TGG | TCT | ATG | TAC | CCA | CTA | CTT | TGG | GAA | AAT | ATG |     | 960  |
| Pro | Gly | Phe | Thr | Gln | Trp | Ser | Met | Tyr | Pro | Leu | Leu | Trp | Glu | Asn | Met |     |      |
| 305 |     |     |     |     | 310 |     |     |     |     | 315 |     |     |     |     | 320 |     |      |
| GGG | ATC | AGC | TAC | CCA | GAA | CTA | ATC | GAG | CGT | TTG | GTT | GAC | CTT | GCC | AAG |     | 1008 |
| Gly | Ile | Ser | Tyr | Pro | Glu | Leu | Ile | Glu | Arg | Leu | Val | Asp | Leu | Ala | Lys |     |      |
|     |     |     |     | 325 |     |     |     |     | 330 |     |     |     |     | 335 |     |     |      |
| GAA | AGT | TTT | GAC | AAG | CGC | GAA | GCG | CAT | TTG | ATA |     |     |     |     |     |     | 1041 |
| Glu | Ser | Phe | Asp | Lys | Arg | Glu | Ala | His | Leu | Ile |     |     |     |     |     |     |      |
|     |     |     | 340 |     |     |     |     | 345 |     |     |     |     |     |     |     |     |      |

( 2 ) INFORMATION FOR SEQ ID NO:2:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Lys | Gln | Thr | Ile | Ile | Leu | Leu | Tyr | Gly | Gly | Arg | Ser | Ala | Glu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Val | Ser | Val | Leu | Ser | Ala | Glu | Ser | Val | Met | Arg | Ala | Val | Asp | Tyr |
|     |     |     | 20  |     |     |     |     | 25  |     |     |     |     | 30  |     |     |
| Asp | Arg | Phe | Thr | Val | Lys | Thr | Phe | Phe | Ile | Ser | Gln | Ser | Gly | Asp | Phe |
|     |     | 35  |     |     |     |     | 40  |     |     |     |     | 45  |     |     |     |
| Ile | Lys | Thr | Gln | Glu | Phe | Ser | His | Ala | Pro | Gly | Gln | Glu | Asp | Arg | Leu |
|     | 50  |     |     |     |     | 55  |     |     |     |     | 60  |     |     |     |     |
| Met | Thr | Asn | Glu | Thr | Ile | Asp | Trp | Asp | Lys | Lys | Val | Ala | Pro | Ser | Ala |
| 65  |     |     |     |     | 70  |     |     |     |     | 75  |     |     |     |     | 80  |

| | | | | | | | | | | | | | | |
|---|---|---|---|---|---|---|---|---|---|---|---|---|---|---|
| Ile | Tyr | Glu | Glu<br>85 | Gly | Ala | Val | Val | Phe | Pro<br>90 | Val | Leu | His | Gly | Pro Met<br>95 |
| Gly | Glu | Asp | Gly<br>100 | Ser | Val | Gln | Gly | Phe<br>105 | Leu | Glu | Val | Leu | Lys<br>110 | Met Pro |
| Tyr | Val | Gly<br>115 | Cys | Asn | Ile | Leu | Ser<br>120 | Ser | Ser | Leu | Ala | Met<br>125 | Asp | Lys Ile |
| Thr | Thr<br>130 | Lys | Arg | Val | Leu | Glu<br>135 | Ser | Ala | Gly | Ile | Ala<br>140 | Gln | Val | Pro Tyr |
| Val<br>145 | Ala | Ile | Val | Glu | Gly<br>150 | Asp | Asp | Val | Thr | Ala<br>155 | Lys | Ile | Ala | Glu Val<br>160 |
| Glu | Glu | Lys | Leu | Ala<br>165 | Tyr | Pro | Val | Phe | Thr<br>170 | Lys | Pro | Ser | Asn | Met Gly<br>175 |
| Ser | Ser | Val | Gly<br>180 | Ile | Ser | Lys | Ser | Glu<br>185 | Asn | Gln | Glu | Glu | Leu<br>190 | Arg Gln |
| Ala | Leu | Lys<br>195 | Leu | Ala | Phe | Arg | Tyr<br>200 | Asp | Ser | Arg | Val | Leu<br>205 | Val | Glu Gln |
| Gly | Val<br>210 | Asn | Ala | Arg | Glu | Ile<br>215 | Glu | Val | Gly | Leu | Leu<br>220 | Gly | Asn | Tyr Asp |
| Val<br>225 | Lys | Ser | Thr | Leu | Pro<br>230 | Gly | Glu | Val | Val | Lys<br>235 | Asp | Val | Ala | Phe Tyr<br>240 |
| Asp | Tyr | Asp | Ala | Lys<br>245 | Tyr | Ile | Asp | Asn | Lys<br>250 | Val | Thr | Met | Asp | Ile Pro<br>255 |
| Ala | Lys | Ile | Ser<br>260 | Asp | Asp | Val | Val | Ala<br>265 | Val | Met | Arg | Gln | Asn<br>270 | Ala Glu |
| Thr | Ala | Phe<br>275 | Arg | Ala | Ile | Gly | Gly<br>280 | Leu | Gly | Leu | Ser | Arg<br>285 | Cys | Asp Phe |
| Phe | Tyr<br>290 | Thr | Asp | Lys | Gly | Glu<br>295 | Ile | Phe | Leu | Asn | Glu<br>300 | Leu | Asn | Thr Met |
| Pro<br>305 | Gly | Phe | Thr | Gln | Trp<br>310 | Ser | Met | Tyr | Pro | Leu<br>315 | Leu | Trp | Glu | Asn Met<br>320 |
| Gly | Ile | Ser | Tyr | Pro<br>325 | Glu | Leu | Ile | Glu | Arg<br>330 | Leu | Val | Asp | Leu | Ala Lys<br>335 |
| Glu | Ser | Phe | Asp<br>340 | Lys | Arg | Glu | Ala | His<br>345 | Leu | Ile | | | | |

( 2 ) INFORMATION FOR SEQ ID NO:3:

( i ) SEQUENCE CHARACTERISTICS:
        ( A ) LENGTH: 1041 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

```
AUGAAACAAA CGAUUAUUCU UUUAUAUGGU GGACGGAGUG CGGAACGCGA AGUCUCUGUC      60

CUUUCAGCUG AGAGUGUCAU GCGUGCGGUC GAUUACGACC GUUUCACAGU CAAGACUUUC     120

UUUAUCAGUC AGUCAGGUGA CUUUAUCAAA ACACAGGAAU UAGUCAUGC UCCGGGGCAA      180

GAAGACCGUC UCAUGACCAA UGAAACCAUU GAUUGGGAUA AGAAAGUUGC ACCAAGUGCU     240

AUCUACGAAG AAGGUGCAGU GGUCUUUCCA GUCCUUCACG GCCAAUGGG AGAAGAUGGC     300

UCUGUUCAAG GAUUCUUGGA AGUUUUGAAA AUGCCUUACG UUGGUUGCAA CAUUUUGUCA     360
```

| | | | | | | |
|---|---|---|---|---|---|---|
| UCAAGUCUUG | CCAUGGAUAA | AAUCACGACU | AAGCGUGUUC | UGGAAUCUGC | UGGUAUUGCC | 420 |
| CAAGUUCCUU | AUGUGGCUAU | CGUUGAAGGC | GAUGAUGUGA | CUGCUAAAAU | CGCUGAAGUG | 480 |
| GAAGAAAAAU | UGGCUUAUCC | AGUCUUCACU | AAGCCGUCAA | ACAUGGGGUC | UAGUGUCGGU | 540 |
| AUUUCUAAGU | CUGAAAACCA | AGAAGAACUC | CGUCAAGCCU | UAAAACUUGC | CUUCCGAUAU | 600 |
| GACAGCCGUG | UCUUGGUUGA | GCAAGGAGUG | AAUGCCCGUG | AAAUUGAGGU | UGGCCUCUUG | 660 |
| GGUAACUACG | AUGUCAAGAG | CACGCUACCU | GGAGAAGUUG | UCAAGGACGU | UGCCUUUUAU | 720 |
| GACUACGAUG | CCAAGUAUAU | UGAUAACAAG | GUUACUAUGG | AUAUUCCUGC | CAAAAUCAGU | 780 |
| GAUGAUGUGG | UGGCUGUCAU | GCGUCAAAAU | GCAGAAACAG | CCUUCCGUGC | CAUUGGUGGC | 840 |
| CUUGGUCUAU | CUCGUUGCGA | UUUCUUCUAU | ACAGAUAAGG | GAGAGAUUUU | UCUCAACGAG | 900 |
| CUCAAUACCA | UGCCAGGUUU | CACCCAGUGG | UCUAUGUACC | CACUACUUUG | GGAAAAUAUG | 960 |
| GGGAUCAGCU | ACCCAGAACU | AAUCGAGCGU | UUGGUUGACC | UUGCCAAGGA | AAGUUUUGAC | 1020 |
| AAGCGCGAAG | CGCAUUUGAU | A | | | | 1041 |